United States Patent [19]

Shene

[11] Patent Number: 4,737,380

[45] Date of Patent: Apr. 12, 1988

[54] ELECTRODE WITH STRETCHED HEAT-SHRINKABLE OUTER INSULATOR

[75] Inventor: William R. Shene, Plattsburgh, N.Y.

[73] Assignee: Monaghan Medical Corporation, Plattsburgh, N.Y.

[21] Appl. No.: 1,690

[22] Filed: Jan. 9, 1987

[51] Int. Cl.[4] .............................................. B05D 5/12
[52] U.S. Cl. .................................. 427/120; 427/118; 156/86; 264/230; 264/DIG. 71
[58] Field of Search .................. 427/120, 118; 156/86; 264/230, DIG. 71

[56] References Cited

U.S. PATENT DOCUMENTS

| | | | |
|---|---|---|---|
| 2,993,820 | 7/1961 | Marshall | 156/86 |
| 4,133,935 | 1/1979 | Dawson | 156/86 |
| 4,168,192 | 9/1979 | Nyberg | 156/86 |
| 4,585,607 | 4/1986 | Krackeler | 156/86 |
| 4,605,003 | 8/1986 | Oinuma | 128/328 |

FOREIGN PATENT DOCUMENTS 944734 12/1963 United Kingdom .................. 156/86

Primary Examiner—Shrive P. Beck
Assistant Examiner—Vi Duong Dang
Attorney, Agent, or Firm—Chilton, Alix & Van Kirk

[57] ABSTRACT

A length of braided wire, having an outside diameter, is selected as is a length of heat-shrinkable tubing which has an initial inside diameter greater than the outer diameter of the braided wire. The braided wire is inserted into the tubing such that, at one end of the tubing, the tubing extends beyond the braided wire. The one end of the tubing is grasped without grasping the braided wire, and the one end is supported against movement in a vertical direction. A weight is attached to the other end of the tubing so that the tubing with the braided wire inserted will extend downwardly from the first end to the other end thereof. Heat is applied to the tubing starting at the one end and moving slowly downwardly to the other end. The heat causes the tubing to shrink and, simultaneously, the weight pulls the tubing downwardly to cause the tubing to stretch so that a tight-fitting insulating cover, having decreased wall thickness, is produced.

8 Claims, 1 Drawing Sheet

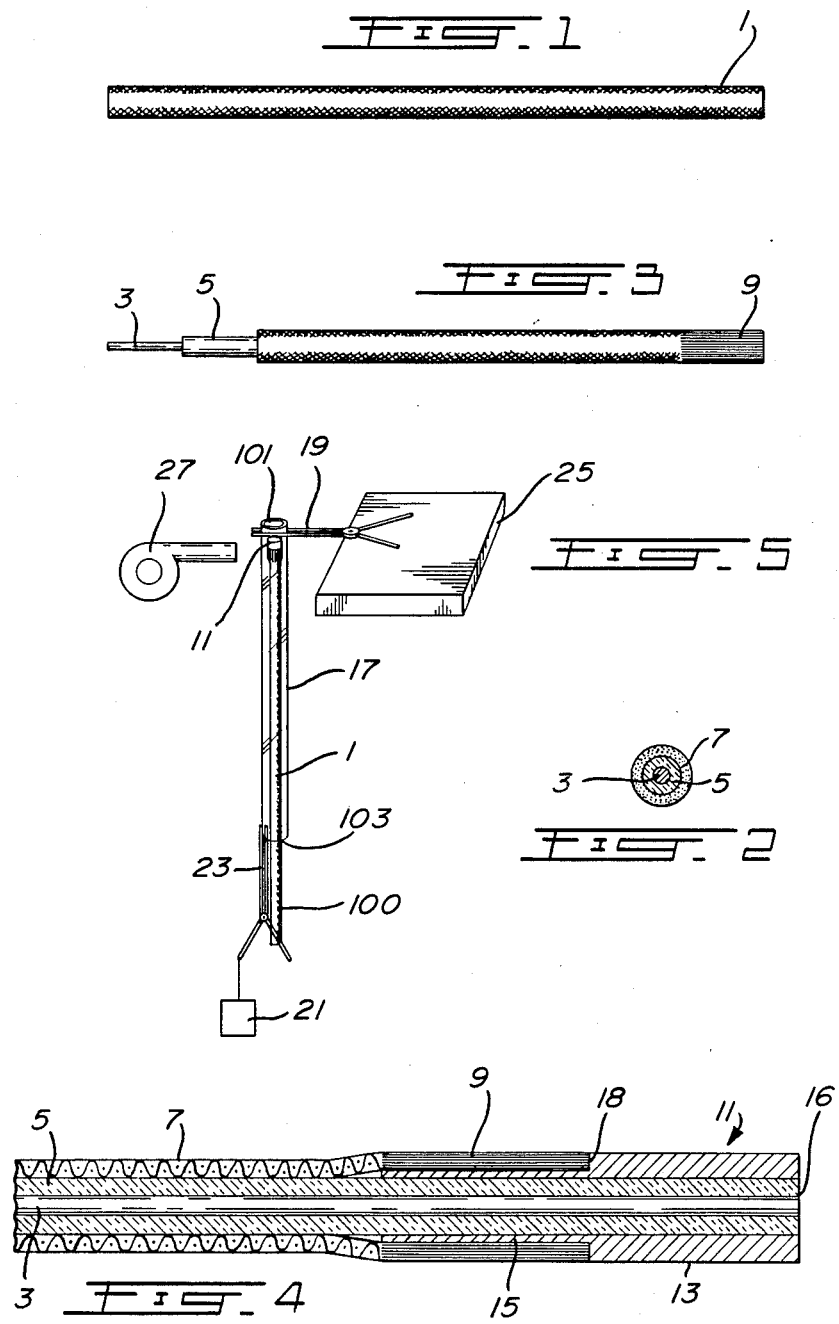

4,737,380

ELECTRODE WITH STRETCHED HEAT-SHRINKABLE OUTER INSULATOR

BACKGROUND OF INVENTION

1. Field of the Invention

The invention relates to a method for providing an insulating cover for a lithotripter electrode. More specifically, the invention relates to such a method which does not substantially increase the outer diameter of the insulated electrode.

2. Description of Prior Art

It is known in the art to use lithotripter electrodes for fragmentation of stones in the urinary and biliary tracts. Such electrodes are inserted into the patient through endoscopes such that the electrode tip is adjacent the stones, and a high potential electric signal is applied to the electrode to cause sparking between the center and outer conductors of the electrode. The resultant hydraulic shock wave fragments the adjacent stone.

As will be appreciated, the electrode must have a very small outer diameter to allow free passage through the small working channel of the endoscope.

In an attempt to construct such an electrode from 3 French braided wire (outer diameter approximately 0.028 to 0.029 inches), which braided wire includes a central conductor surrounded by an insulator and an outer coat of braided conductor strands (the braided coat being braided from four strands of interwoven copper conductor approximately 0.002 inches per strand), the problem arises of providing an insulating cover for the braided wire.

One solution which has presented itself is to encase the braided wire in a heat-shrinkable tubing, e.g. tubing identified by the trade mark FIT, specifically, FIT-350 Insulated Kynar tubing. However, such tubing has a wall thickness of 0.010 inches before the tubing is shrunk, and the wall thickness will increase when the tubing is shrunk. Thus, the outer diameter of the insulated braided wire would be increased by at least 0.02 inches. Such an increase is, of course, far too large to be acceptable.

Dipping the braided wire in a melted insulation and then letting it dry would provide an irregular outer surface of the insulated braided wire and would also provide an unacceptably large outer diameter.

Traditional approaches for applying an insulating cover to an electric conductor are illustrated in U.S. Pat. No. 3,471,327, Gerland et al; Oct. 7, 1969, U.S. Pat. No. 4,183,888, Mutzke, Jan. 15, 1980, U.S. Pat. No. 4,497,849, Hughes et al, Feb. 5, 1985, and U.S. Pat. No. 4,521,363, Vogel, June 4, 1985. The U.S. Pat. No. 3,471,327 teaches a dipping method while the remainder of the patents are directed at extrusion methods. None of these methods would be acceptable for the production of lithotripter electrodes with an insulated covering.

SUMMARY OF INVENTION

It is therefore an object of the invention to provide a method for providing an insulating covering for a lithotripter electrode.

In accordance with the invention there is provided a method for producing an insulator covered lithotripter electrode which includes the steps of selecting a length of braided wire having an outer diameter and selecting a length of heat-shrinkable tubing having an initial inner diameter greater than the outer diameter of the braided wire. The braided wire is inserted into the tubing such that, at one end of the tubing, the tubing extends beyond the braided wire. One end of the tubing is grasped without grasping the braided wire. A weight is attached to the other end of the tubing, whereby, the tubing with the braided wire inserted therein, will extend downwardly from the first end to the other end thereof. Heat from a heat source is applied to the tubing, the heat source being located initially at the first end of the tubing. The heat from the heat source causes the tubing to shrink and, simultaneously, the weight pulls the tubing downwardly to cause the tubing to stretch and thereby increase the length thereof and decrease the wall thickness of the tubing. The heat source is moved downwardly as the tubing stretches so that the tube shrinks onto the braided wire to provide a tight-fitting insulator cover, and the tube stretches to decrease the wall thickness thereof such that the outer diameter of the insulated wire is not substantially greater than the outer diameter of the braided wire without insulation.

BRIEF DESCRIPTION OF DRAWINGS

The invention will be better understood by an examination of the following description, together with the accompanying drawings, in which:

FIG. 1 shows a length of braided wiring;

FIG. 2 is an end view of FIG. 1;

FIG. 3 illustrates the braided wire after several steps of the process have been carried out;

FIG. 4 illustrates changes after still more steps have been carried out; and

FIG. 5 illustrates a set-up for the final steps of the method.

DESCRIPTION OF PREFERRED EMBODIMENTS

Referring to the drawings, a braided wire, illustrated generally at 1, comprises a central conductor 3, a surrounding insulator 5 and the outer coat of braided strands 7.

In carrying out the method, a length of braided wire, for example, a length of 135 cm, is selected. The selected length is then subjected to a high voltage potential test to check for insulation integrity of the center conductor. If an insulation defect exists, then the selected length is rejected.

After the length has passed the high voltage potential test, the inner conductor 3 and the surrounding insulation 5 is slid out of one end of the outer coat 7 for a length of approximately 1 inch. At the opposite end, the braid of the outer coat is combed until the conductors are parallel with each other. A minimum length of $\frac{1}{4}$ inch should be so combed. The length of braided wire will then appear as illustrated in FIG. 3 wherein 9 is the length of parallel combed copper strands.

The center conductor and insulator are then slid back into the outer coat of braid and then out the other end for a length of approximately 1 inch. A tip 11, illustrated in FIG. 4, is then mounted onto the protruding end of the selected length of inner conductor wire. As seen in FIG. 4, the tip comprises a large outer diameter portion 13 and a small outer diameter portion 15. The central conductor 3 and surrounding insulation 5 are inserted into the central opening 16 of the tip, and the small outer diameter portion of the tip is slid under the parallel combed strands 9 of braiding until the braiding 9 abuts the step 18 of the tip and the inner conductors and insulator 5 protrude from the central opening 16. It is necessary to ensure that the strands do not overlap the step. In addition, the parallel strands of the braid must be kept parallel to each other and overlapping of braids by each other must be avoided.

The selected braid of wire is then inserted into a heat-shrinkable transparent tubing 17 as shown in FIG. 5. In this regard, the end 100 of the braided wire 1 is inserted through the end 101 of tubing 17, and the braided wire is moved downwardly until the end 100 extends beyond the other end 103 of the tubing. The tip 11 is fully within the tubing 17 in that it is below the end 101 of the tubing 17. The tip 11 should be approximately 2 inches below the end 101 of the tubing.

At this point, the combed portion 9 of the braiding should be checked for correct position relative to the tip and to insure that there are no overlapping strands of combed braid. If any defects have been formed, then the wire 1 should be pulled out of the tubing and the combed portion 9 should be recombed and repositioned.

The tubing 17 is then grasped by a grasping means 19 below end 101 but above the tip 11 so that the braided wire is not grasped by the grasping means 19. Any grasping means could be used, but hemostats are preferred.

A weight 21 is applied to the other end 103 of the heat-shrinkable tubing 17. Preferably, the weight 21 is applied by attaching it to grasping means 23, which, once again, are preferably hemostats, and attaching the other end of the hemostats to the end 103 of the heat-shrinkable tubing 17. A weight of approximately 170 grams is suitable for this purpose.

The grasping means 19 are fixedly supported against vertical movement on, for example, a bench top 25. Thus, the top end 101 of the tubing 17 is fixed at a vertical location.

Heat is then applied to the tubing by a heat source 27. The heat is applied first at the top end 101 of the tubing and the heat source is moved slowly downwardly so that the heat is applied at continuously lower portions of the shrinkable tubing. When the heat is applied, the tubing will, of course, shrink. In addition, because of the weight 21 applied at the bottom end 103 of the tubing, the tubing will also stretch downwardly, the stretch occurring at the heated portion.

By the proper and appropriate application of weight and rate of downward movement, which weight and rate of downward movement are a function of the characteristics of the particular tubing selected, a tight-fitting (due to shrinkage) insulating cover will be provided. The wall thickness of the insulating cover will be reduced relative to the wall thickness before shrinkage in view of the stretching caused by the weight 21. Thus, the outer diameter of the insulated braided wiring is not substantially increased relative to the outer diameter of the braided wire without insulation.

As the heat-shrinkable tubing is stretched during the process, the initial length of the tubing should be less than the length of the braided wire.

The tubing is then trimmed from both ends of the covered braided wire, and approximately 1 mm of heating-shrinkable tubing is removed from the tip end of the insulated braided wire. The tip is then ground as flat as possible, perpendicular to the long axis of the tip, making sure that the center conductor is centered in the tip and the inner insulation 5 is continuous around the inner conductor 3. The entire length of the assembly is checked for proper outer diameter dimension and uniformity.

The insulated electrode is then test-fired, and, if the test is successful, a connector is mounted on the end of the insulated braided wire opposite from the tip end leaving approximately 120 cm of useable length.

Because the tubing is stretched and shrunkfitted, the braid which overlies the small diameter portion of the tip is held tightly against the tip to mechanically hold the tip in position and to provide good electrical contact between the braid and the tip. As this is accomplished without soldering or other similar process, the diameter is maintained in the area of the small diameter portion of the tip.

Although a particular embodiment has been illustrated, this was for the purpose of describing, but not limiting, the invention. Various modifications, which will come readily to the mind of one skilled in the art, are within the scope of the invention as defined in the appended claims.

I claim:

1. A method for producing an insulator covered lithotripter electrode, comprising:
   selecting a length of braided wire having an outer diameter;
   selecting a length of heat-shrinkable tubing having an initial inner diameter greater than the outer diameter of said braided wire;
   inserting said braided wire into said tubing such that, at one end of said tubing, said tubing extends beyond said braided wire;
   grasping said one end of said tubing without grasping said braided wire;
   attaching a weight to the other end of said tubing, whereby, said tubing with said braided wire inserted therein, will extend downwardly from said first end to said other end thereof;
   applying heat from a heat source to said tubing, said heat source being located initially at said first end of said tubing;
   whereby, said heat from said heat source causes said tubing to shrink and, simultaneously, said weight pulls said tubing downwardly to cause said tubing to stretch and thereby increase the length thereof and decrease the wall thickness of said tubing;
   moving said heat source downwardly as said tubing stretches;
   whereby, said tube shrinks onto said braided wire to provide a tight-fitting insulator cover, and said tube stretches to decrease the wall thickness thereof such that the outer diameter of said insulated wire is not substantially greater than the outer diameter of said braided wire without insulation.

2. A method as defined in claim 1 wherein said braided wire comprises an outer coat of braided conductor strands;
   and including the step, prior to inserting said braided wire into said tubing, of combing one end of said outer coat to produce a combed portion of parallel conductor strands at said one end of said braided wire.

3. A method as defined in claim 2 wherein said braided wire comprises a central conductor and surrounding insulator;
   and including the step, prior to inserting said braided wire into said tubing, of installing a tip onto said one end of said braided wire;

said tip comprising a large outer diameter portion and a small outer diameter portion and a central opening;

sliding a portion of said central conductor and surrounding insulator out of said coating at said one end of said braided wire;

said tip being installed on said one end of said braided wire such that said small outer diameter portion precedes said large outer diameter portion and said portion of said central conductor and surrounding insulator extends through said central opening of said tip;

said combed portion overlying said small outer diameter portion to provide an electrical connection while maintaining a small diameter.

4. A method as defined in claim 3 wherein, in the step of inserting said braided wire into said tubing, said other end of said braided wire is inserted through one end of said tubing and pushed through until said tip is fully enclosed by said tubing and said one end of said braided wire is below said one end of said tubing.

5. A method as defined in claim 4 wherein said one end of said tubing is grasped by hemostats;

and including the step of supporting said hemostats, and therefore said one end of said tubing, against movement in a vertical direction.

6. A method as defined in claim 5 and including trimming excess tubing from both ends of said braided wire.

7. A method as defined in claim 6 and including cutting a small portion of tubing from said one end and grinding said tip flat.

8. A method as defined in claim 7 wherein the selected length of heat-shrinkable tubing is initially shorter than the selected length of braided wire.

* * * * *